(12) United States Patent
Chen et al.

(10) Patent No.: US 10,307,543 B2
(45) Date of Patent: Jun. 4, 2019

(54) POWER PACK ASSEMBLY FOR A MEDICAMENT DELIVERY DEVICE

(71) Applicant: Carebay Europe Ltd., Sliema (MT)

(72) Inventors: Hsueh-Yi Chen, New Taipei (TW);
Jung-Chien Chou, Changhua (TW);
Jyun-An Yao, Pingtung County (TW)

(73) Assignee: SHL Medical AG, Zug (CH)

( * ) Notice: Subject to any disclaimer, the term of this patent is extended or adjusted under 35 U.S.C. 154(b) by 164 days.

(21) Appl. No.: 15/517,654

(22) PCT Filed: Sep. 28, 2015

(86) PCT No.: PCT/EP2015/072257
§ 371 (c)(1),
(2) Date: Apr. 7, 2017

(87) PCT Pub. No.: WO2016/055295
PCT Pub. Date: Apr. 14, 2016

(65) Prior Publication Data
US 2017/0304548 A1    Oct. 26, 2017

(30) Foreign Application Priority Data
Oct. 9, 2014    (SE) ...................................... 1451208

(51) Int. Cl.
*A61M 5/20* (2006.01)
*A61M 5/32* (2006.01)
*A61M 5/315* (2006.01)

(52) U.S. Cl.
CPC ............ *A61M 5/3157* (2013.01); *A61M 5/20* (2013.01); *A61M 5/2033* (2013.01);
(Continued)

(58) Field of Classification Search
CPC ...... A61M 2005/2013; A61M 5/31571; A61M 5/20; A61M 5/2033; A61M 2005/2073; A61M 2005/208
See application file for complete search history.

(56) References Cited

U.S. PATENT DOCUMENTS

| 2005/0101919 A1* | 5/2005 | Brunnberg .......... A61M 5/2033 604/197 |
| 2012/0209192 A1* | 8/2012 | Alexandersson ... A61M 5/2033 604/135 |
| 2016/0367763 A1 | 12/2016 | Tschirren et al. |

FOREIGN PATENT DOCUMENTS

| CH | 707216 A2 | 4/2014 |
| EP | 2596826 A1 | 5/2013 |

(Continued)

OTHER PUBLICATIONS

Search Report Issued in Taiwanese Patent Application No. 104132842 dated Feb. 17, 2017.

*Primary Examiner* — Amber R Stiles
*Assistant Examiner* — Nicholas J Chidiac
(74) *Attorney, Agent, or Firm* — McDonnell Boehnen Hulbert & Berghoff LLP

(57) ABSTRACT

A power pack assembly for a medicament delivery device, the power pack comprising a plunger rod (64) extending along a longitudinal axis (L) and having a proximal and an opposite distal ends, an actuator (90) provided with a holding element (96) and configured to interact with a corresponding holding element on the plunger rod (64), a first force element (68) arranged to exert a force on the plunger rod; an actuator sleeve mechanism (119) arranged to releasably lock said holding element (96) in engagement with the corresponding holding element of said plunger rod (64) such as to hold said first force element (68) in a tensioned state. The invention is characterized in that said (Continued)

actuator sleeve mechanism (119) comprises an actuator cap (134) configured to hold said holding element (96) in engagement with the corresponding holding element of said plunger rod (64) and an actuator sleeve (120) interconnected with said actuator cap (134) such that in relation to the actuator (90), said actuator cap (134) is moved a shorter distance than the actuator sleeve (120) when said actuator sleeve is distally displaced in relation to the distal housing part.

20 Claims, 12 Drawing Sheets

(52) U.S. Cl.
CPC ..... *A61M 5/3202* (2013.01); *A61M 2005/206* (2013.01); *A61M 2005/208* (2013.01); *A61M 2205/581* (2013.01)

(56) References Cited

FOREIGN PATENT DOCUMENTS

| | | | |
|---|---|---|---|
| WO | 2005044348 | A1 | 5/2005 |
| WO | 2011043714 | A1 | 4/2011 |
| WO | 2011162686 | A1 | 12/2011 |

* cited by examiner

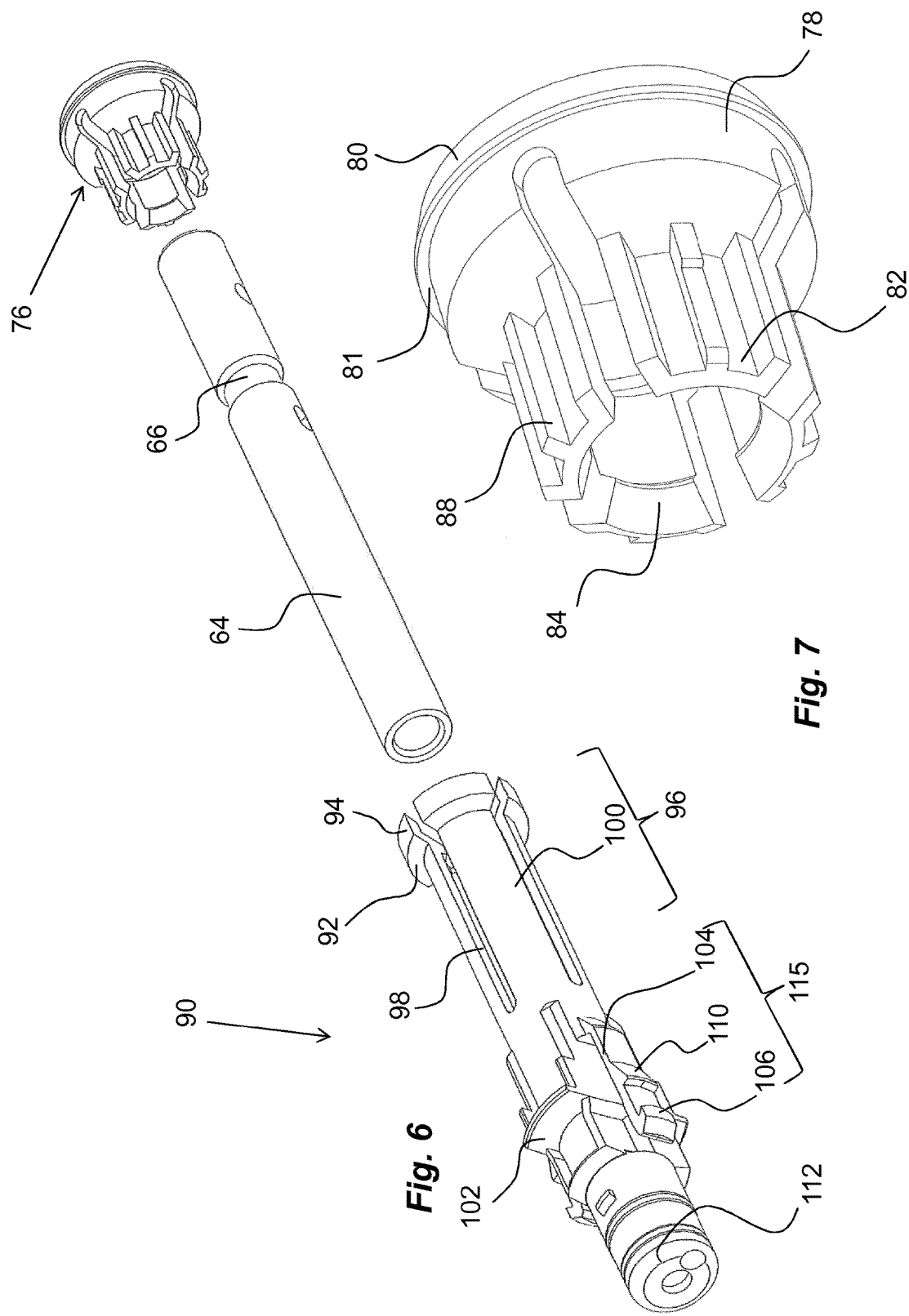

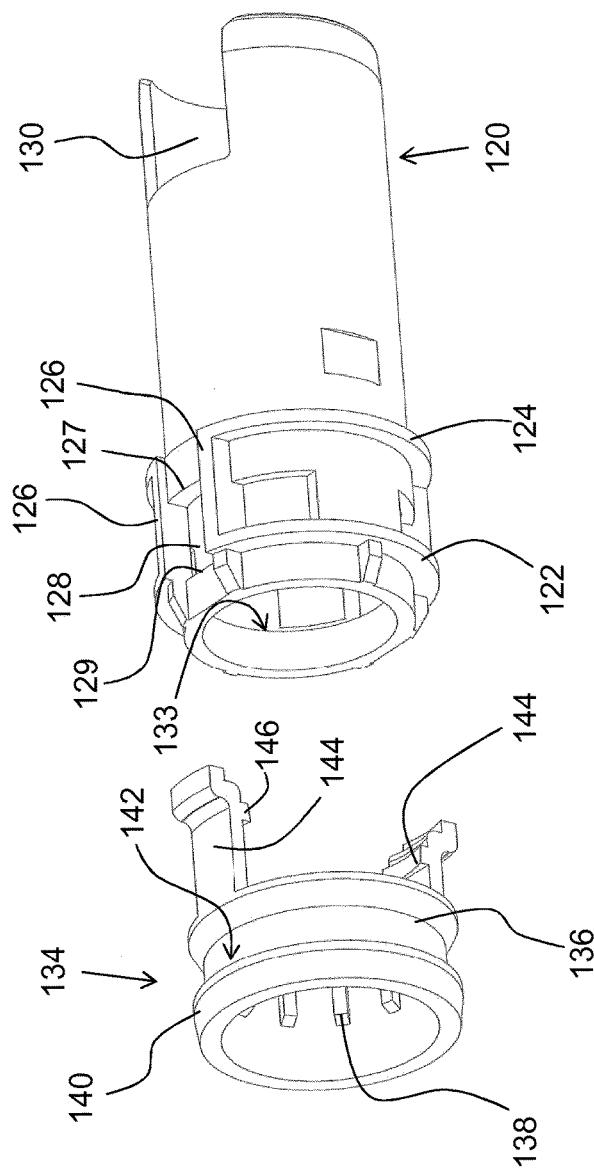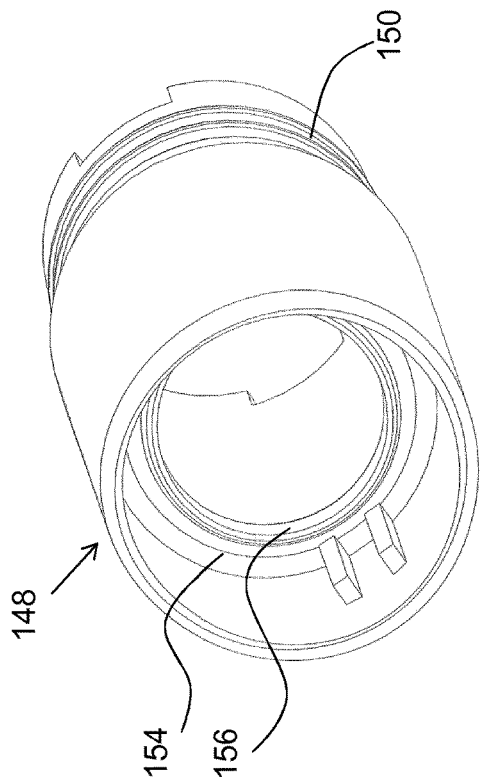

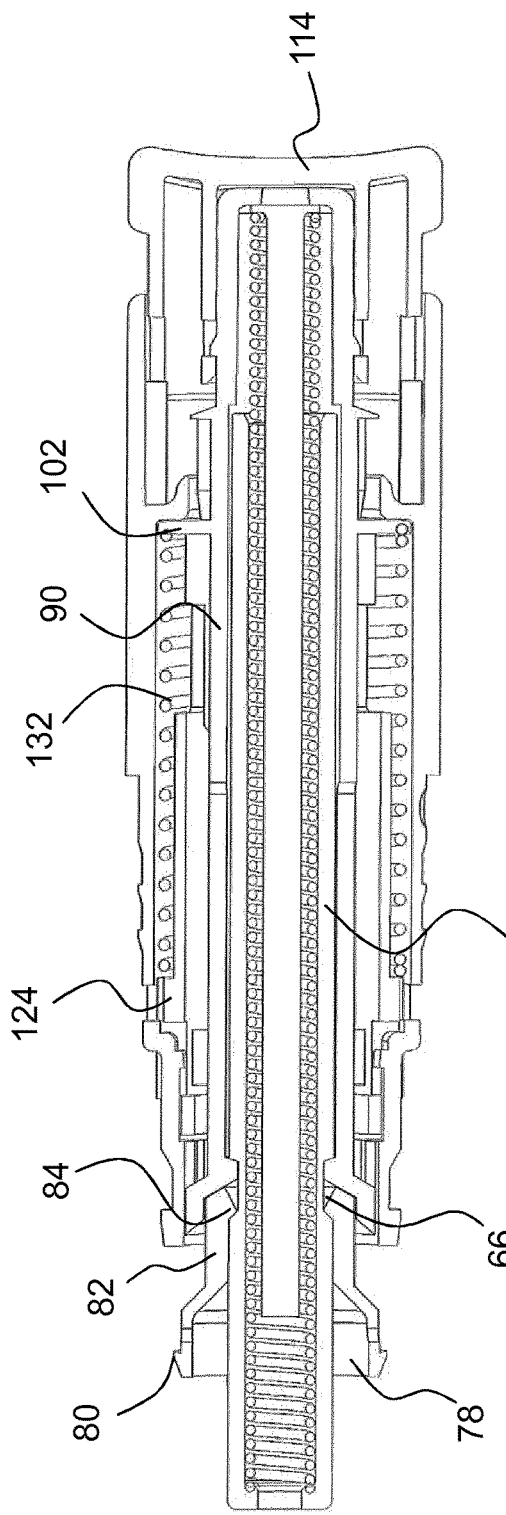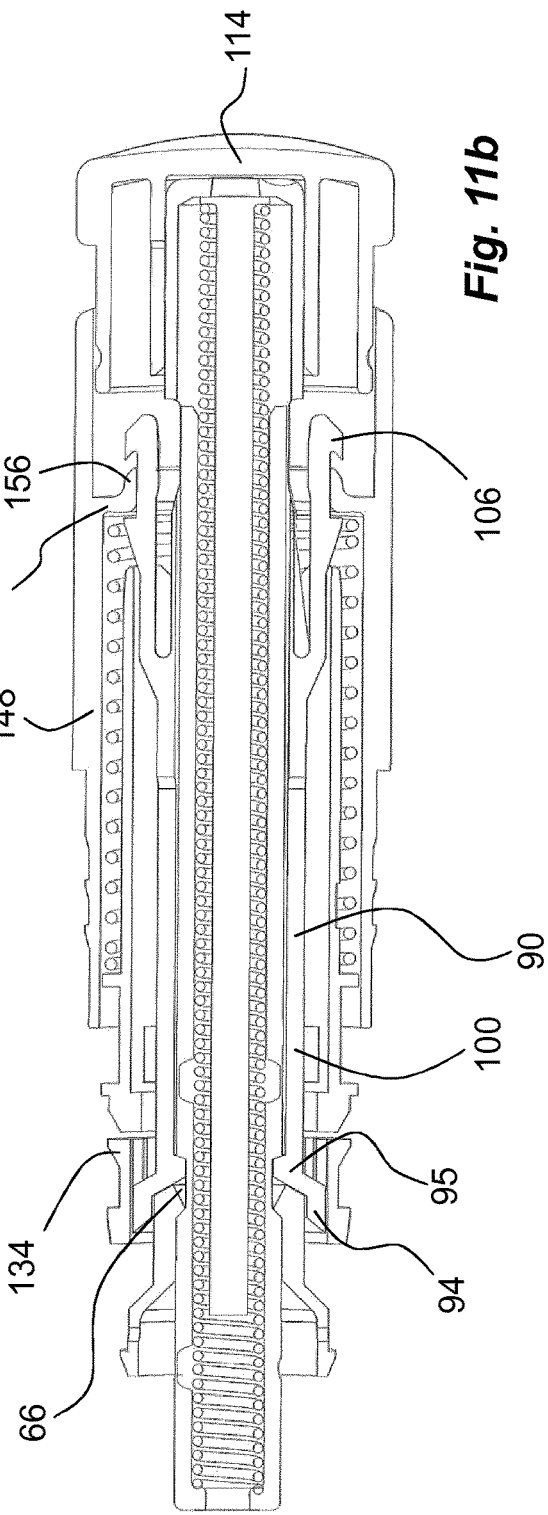

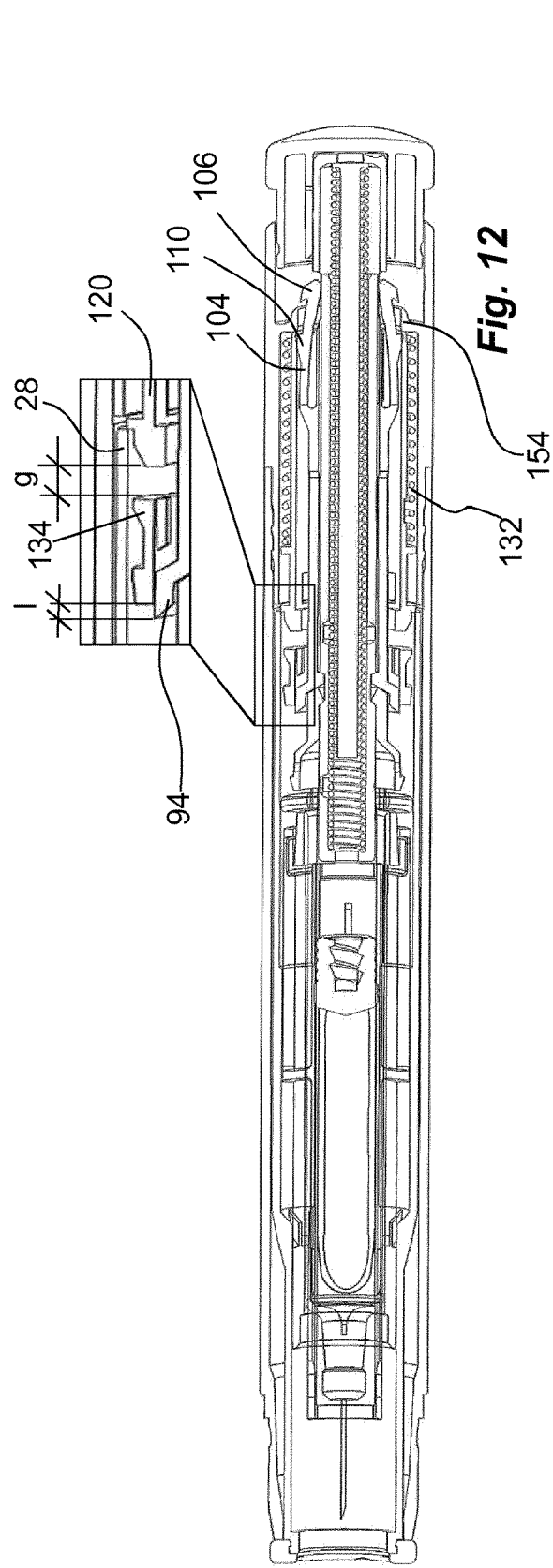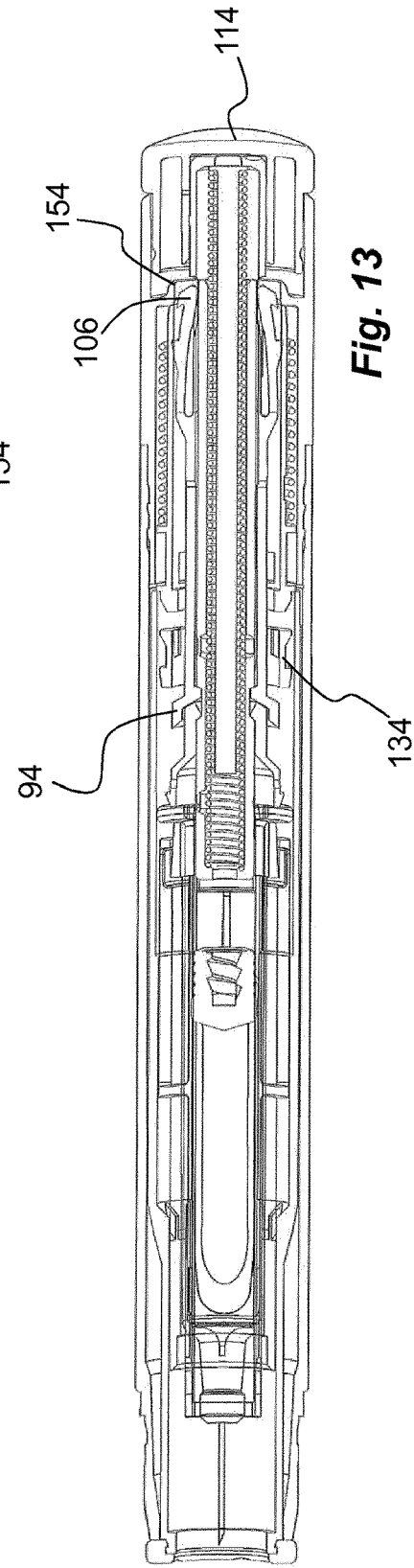

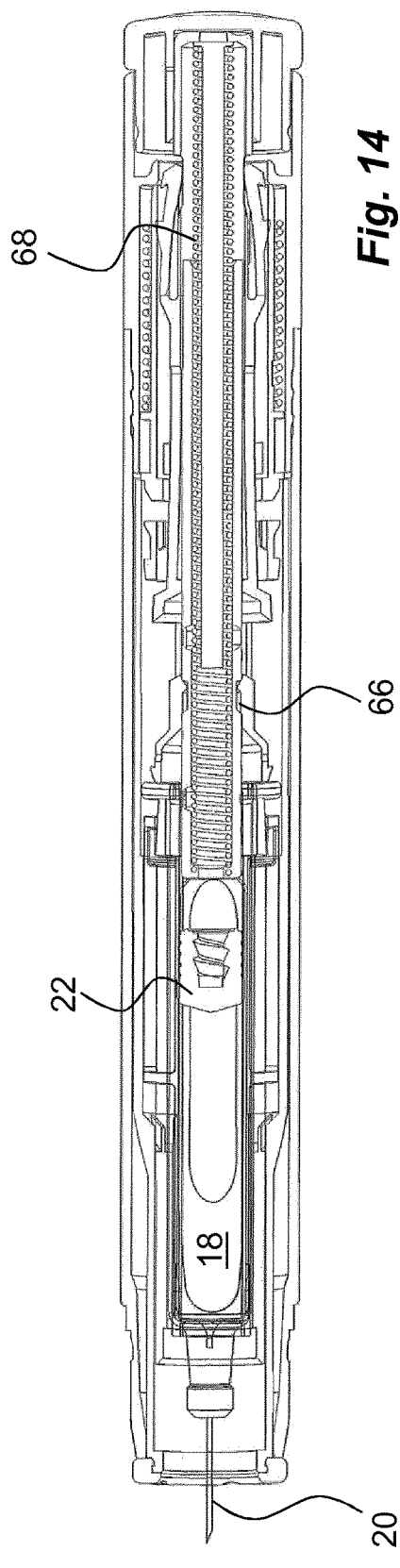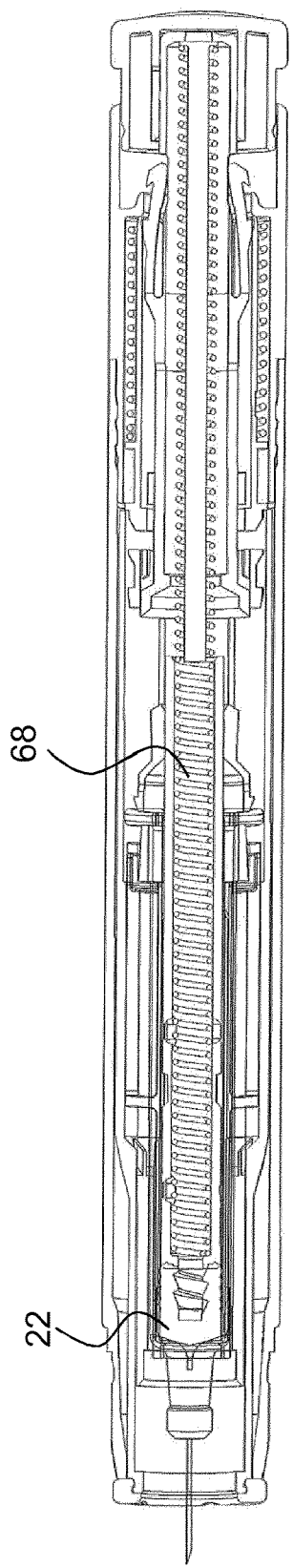

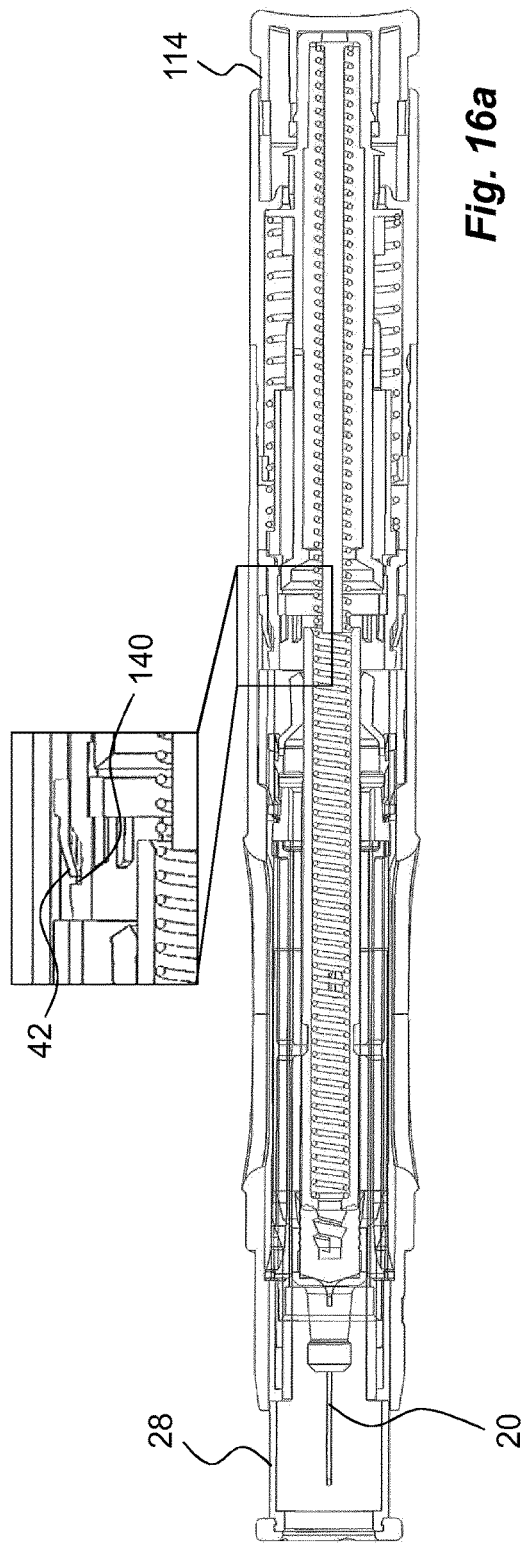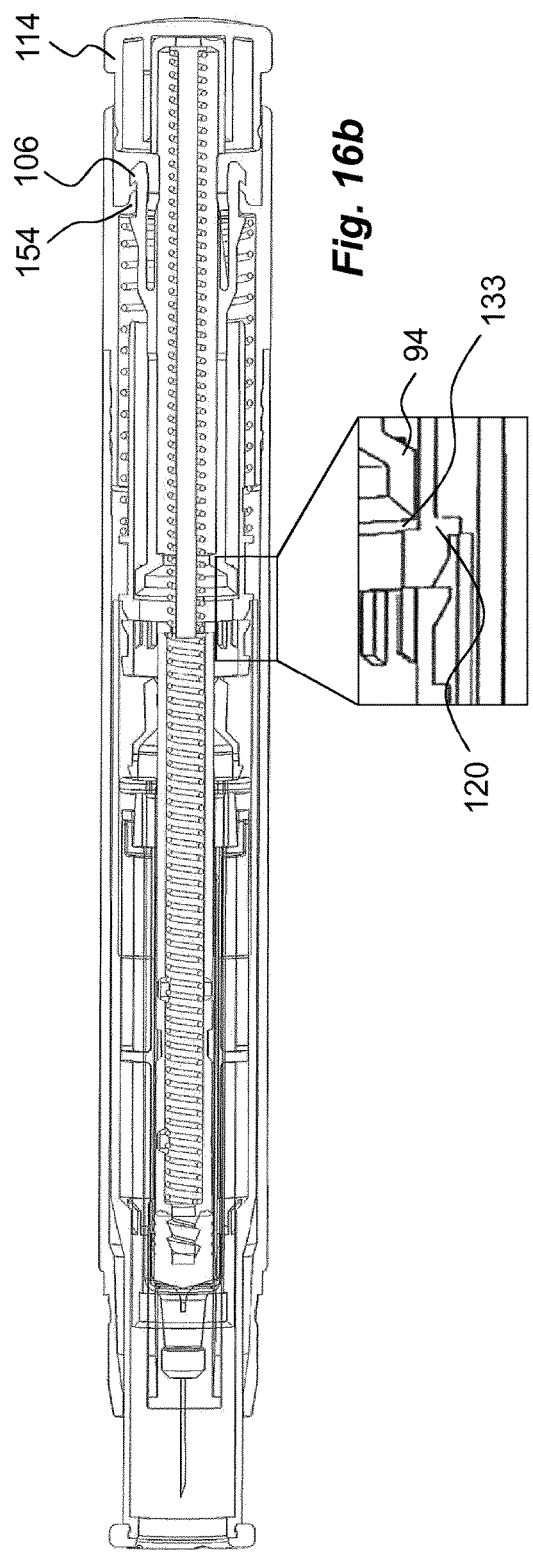

POWER PACK ASSEMBLY FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2015/072257 filed Sep. 28, 2015, which claims priority to Swedish Patent Application No. 1451208-1 filed Oct. 9, 2014. The entire disclosure contents of these applications are herewith incorporated by reference into the present application.

TECHNICAL AREA

The present invention relates to power pack assembly for a medicament delivery device.

BACKGROUND OF INVENTION

Many devices on the market have been developed to be handled by persons that are not trained medical staff. Such devices have to be very simple and intuitive to use. Therefore, many devices have been arranged with a number of automatic functions, such as penetration, injection, withdrawal, shielding of the medicament delivery member, etc.

A device that has been on the market for some time is disclosed in WO2005044348A1. It comprises an auto injector having a number of automatic features that render the device easy and intuitive to use. A main drive spring is used for first performing a penetration sequence, followed by a dose delivery sequence. The device is arranged with a two-step function in that a needle shield has to be pressed against a dose delivery site in order to unlock activation of the device. That is, the movement of the needle shield in the distal direction inside the device will unlock an actuator function that can be activated by an actuator button. When the dose delivery has been performed and the device is removed from the dose delivery site, a needle shield spring acts on the needle shield for covering the injection needle after use. The needle shield spring also acts to lock the actuator function again, should the device be removed from the dose delivery site before activation.

For some types of drugs, the device requires a stronger drive spring than originally developed for the device. However, a stronger drive spring has resulted in some functional issues due to increased friction between parts, which is due to the increased force from the drive spring. In some instances, the needle shield has not been able to overcome the increased friction, causing the actuator function to remain unlocked if the device is removed from the dose delivery site before activation. In such a situation the device may be unintentionally activated if the actuator button should be operated without the device being pressed against a dose delivery site.

BRIEF DESCRIPTION OF INVENTION

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient.

The aim of the present invention is to remedy the drawbacks of the state of the art devices. This aim is obtained by a power pack assembly for a medicament delivery device according to the independent claim. Preferable embodiments of the invention form the subject of the dependent patent claims.

The power pack assembly described comprises a plunger rod extending along a longitudinal axis and has a proximal and an opposite distal end, an actuator provided with a holding element and configured to interact with a corresponding holding element on the plunger rod, a first force element arranged to exert a force on the plunger rod, an actuator sleeve mechanism arranged to releasably lock said holding element in engagement with the corresponding holding element of said plunger rod such as to hold said first force element in a tensioned state. The actuator sleeve mechanism comprises an actuator cap configured to hold said holding element in engagement with the corresponding holding element of said plunger rod, and an actuator sleeve interconnected with said actuator cap such that said actuator cap is moved a shorter distance in relation to the actuator than the actuator sleeve when said actuator sleeve is distally displaced in relation to the distal housing part.

The plunger rod is arranged to interact with a medicament container of the medicament delivery device. In that respect, the medicament container may comprise at least one stopper movable inside the medicament container. When the stopper is moved by the plunger rod, a dose of medicament may be expelled through a medicament delivery member. The medicament delivery member may be an injection needle, a nozzle, a mouthpiece or a nebulizer, etc. Further, a force element may be arranged to force said plunger rod to act on the medicament container for expelling a dose of medicament. The force element may be a spring of a certain type, such as a compression spiral spring, a clock spring, a torsion spring, a gas spring, etc.

Preferably the actuator sleeve mechanism is arranged to interact with the plunger rod, such as to hold the first force element in a tensioned state before activation of the device. The actuator cap and the actuator sleeve may preferably be slidably arranged in relation to each other. The actuator cap and the actuator sleeve may preferably be slidable along the longitudinal axis.

The actuator sleeve mechanism further comprises a second force element arranged between said actuator and said actuator sleeve. The second force element is thus configured to exert a force on said actuator sleeve. The force exerted by the second force element is preferably to urge the actuator sleeve towards the proximal end.

Further, the power pack assembly comprises a distal housing part in which the actuator is slidably arranged. The actuator is preferably slidable along the longitudinal axis. Thus, the actuator, the actuator cap and the actuator sleeve are preferably slidable in relation to the distal housing part.

According to a favourable solution, the actuator cap and the actuator sleeve may be arranged longitudinally slidable in relation to each other. The actuator cap may interact with the holding elements, and the actuator sleeve may interact with a medicament delivery member guard of the medicament delivery device. The actuator cap is preferably interconnected with the actuator sleeve such that the actuator cap moves a shorter distance in the distal direction than the actuator sleeve when the medicament delivery member guard is pressed against a dose delivery site. More particularly, said actuator cap and said actuator sleeve are interconnected by a distally extending tongue provided with a radial inwardly directed protrusion which fits into a compartment on the actuator sleeve, wherein said compartment is configured to allow a relative displacement between the actuator cap and the actuator sleeve from a first position in which the radial inwardly directed protrusion is in contact with a distal end surface of the compartment to a second position in which the radial inwardly directed protrusion is moved in contact with a proximal end surface of the compartment, upon distal displacement of the actuator sleeve.

Where prior art needs to overcome frictional resistance at two interfaces simultaneously, namely between the actuator sleeve and the holding element and between the actuator sleeve and the locking member. The solution of the present application divides the resistance into a first and a second separate step. In the first step, the friction at the interface between the actuator sleeve and the locking member is overcome. In the second step, the friction between the actuator cap and the holding element is overcome.

Thus, when a user places the medicament delivery device at an injection site, the medicament delivery member guard is distally displaced, pushing the actuator sleeve along in the distal direction to overcome the first frictional resistance between the actuator sleeve and the locking member. After moving a distance g, the first resistance is substantially overcome because the locking member has flexed radially inwards, out of the way of a distally directed edge of the actuator sleeve, significantly reducing the longitudinal component of the frictional force at the interface. Also, at this point, the actuator cap is engaged to the actuator sleeve and is brought along in the distal direction by the actuator sleeve. During this continued movement, the second frictional resistance is overcome.

Accordingly, the risk of malfunction is reduced when the user removes the device, because the frictional resistances are again overcome separately, in the same order. First the medicament delivery member guard and the actuator sleeve move proximally, overcoming the first frictional resistance. Subsequently, after moving the distance g in the proximal direction, the actuator cap is engaged to the actuator sleeve and is brought along in the proximal direction by the actuator sleeve, overcoming the second frictional resistance.

The medicament delivery device may further comprise a manually operated actuator button. The actuator button may preferably be interconnected with the actuator such that when the actuator is activated by proximally pressed, operation of the actuator button will release the plunger rod, which is held in a the tensioned state, thereby expelling a dose of medicament. Thus, according to the description of the present embodiment, two distinct operations are required in order to activate the device for the delivery of a dose of medicament; firstly the pressing of the device against a dose delivery site and secondly a manual pressing of the actuator button. However, it is also considered other embodiments where it is not necessary to have these distinct operations.

Thus, in order to increase the safety of the device, it may further comprise a locking mechanism capable of locking the actuator button i.e. the actuator until the actuator cap of the actuator mechanism has moved distally a certain distance. Thereby, the actuator button i.e. actuator is locked when the device is not pressed against a dose delivery site.

According to a feasible solution, the actuator comprises a locking member configured to interact with a corresponding locking member of the distal housing part for locking a proximal displacement of said actuator until said actuator sleeve is distally displaced in relation to the distal housing part. The actuator sleeve is configured to interact with the locking member of the actuator when said actuator sleeve is distally displaced such that the actuator is allowed to be proximally displaced. The proximal displacement of the actuator allows the holding element of the actuator to be released from the actuator cap such that the engagement between the holding element of the actuator and the corresponding holding element of the plunger rod is released, whereby said first force element is released from the tensioned state forcing the plunger rod to be proximally displaced. The radially extending inwardly directed ledge is arranged at the inner end of the generally radially flexible tongue of said actuator.

According to a feasible solution, the locking member of the actuator comprises a radial flexible tongue arranged with an outwardly directed hook at the outer end, and a protrusion with an inclined surface extending a distance along the radially flexible tongue; and wherein the corresponding locking member of the distal housing part comprises an annular distally directed ledge. Also, the holding element comprises a generally flexible tongue having an inclined transition surface which meets with a band-shaped part with enlarged diameter and an radially extending inwardly directed ledge, and wherein the corresponding holding element of said plunger rod comprises a circumferential groove, having a mutual shapes so as to fit the radially extending inwardly directed ledge in said circumferential groove.

In order to obtain a release function, the actuator sleeve comprises a distally directed edge arranged to interact with the inclined surface whereby, upon distal displacement of said actuator sleeve, the radially flexible tongue with the hook is moved radially inwards such that the outwardly directed hook is free to pass inside the annular distally directed ledge of the distal housing part. Further, the actuator cap comprises a ring-shaped body having an inner diameter generally corresponding to the radial extension of the holding element in the area of the band-shaped part.

The medicament delivery device described comprises a housing, which housing is arranged to accommodate a medicament container. The housing may have a number of different features or shapes according to desired function and appearance. The housing may also comprise a number of housing parts that are interconnected to each other, either releasably or permanently. The medicament container may further have a number of designs or features. It could be a syringe or a cartridge. It may further be a single-chamber or a multi-chamber medicament container.

In order to be able to return the medicament delivery member guard to its initial position, it may be arranged with a force element operably connected to the actuator sleeve and arranged to return said actuator sleeve in a proximal direction when the device is removed from the medicament delivery site.

These and other features and advantages with the present invention will become apparent from the following detailed description and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
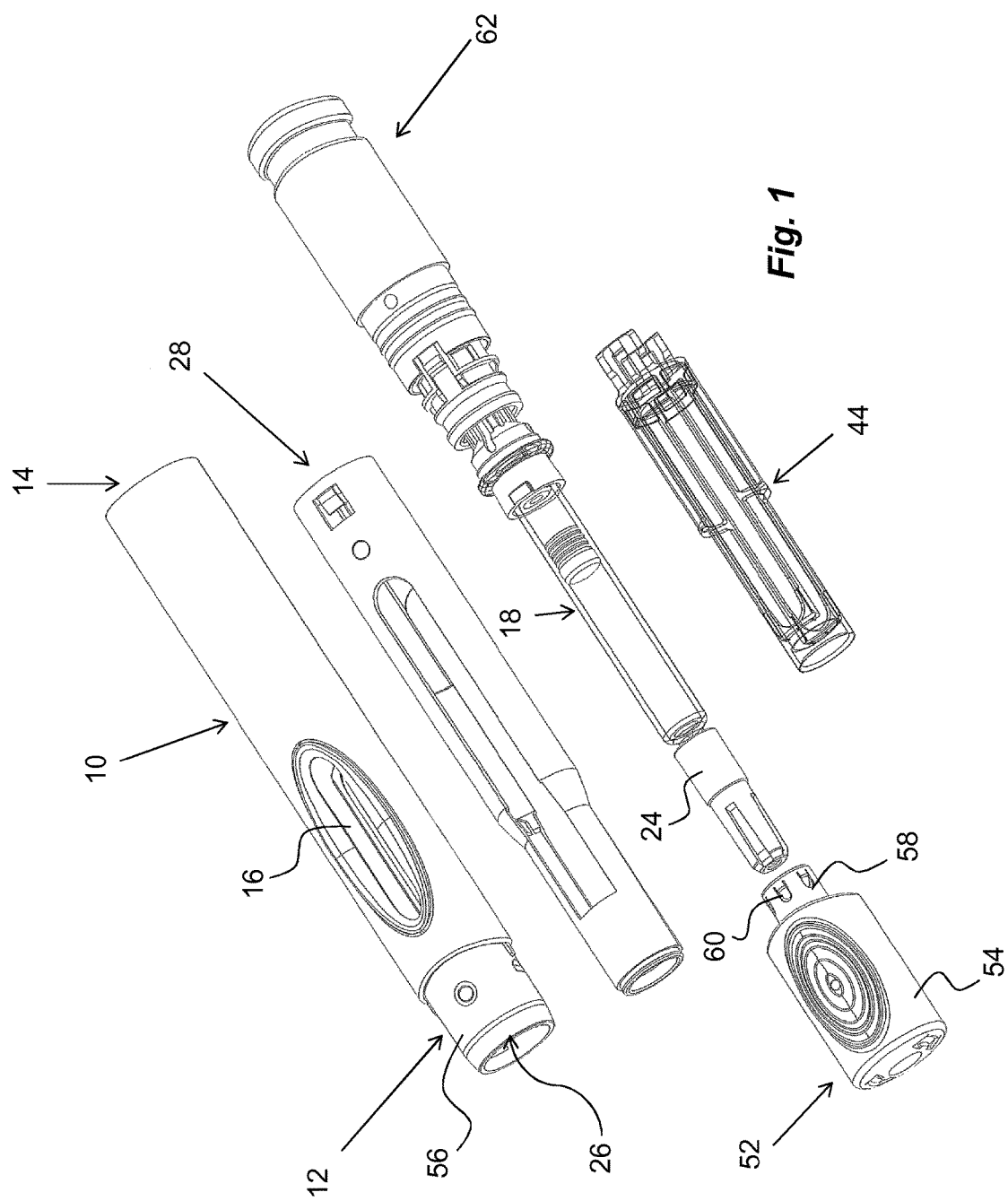
FIG. 1 is an exploded view of an embodiment of a medicament delivery device, FIG. 2a,b are longitudinal cross-sectional views of the device of FIG. 1, FIGS. 3 and 4 are detailed views of components comprised in the device of FIG. 1.

An embodiment of a medicament delivery device is shown in the drawings, comprising a generally tubular proximal housing part 10. The proximal housing part 10 has a proximal end 12 and a distal end 14. The proximal housing part 10 is provided with elongated openings or windows 16 for viewing a medicament container 18, FIG. 1. The medicament container 18 is in the embodiment shown arranged with a medicament delivery member 20, FIG. 2, fixed to the medicament container and a movable stopper 22 inside the medicament container 18. It is however to be understood that the medicament delivery member may also be a separate part that is attachable to the medicament container by appropriate connection elements such as threads, bayonet fittings or luer connections, etc. Further, the medicament delivery member 20 is protected by a medicament delivery member shield 24, which in the embodiment shown is a so called rigid needle shield or RNS. It is however to be understood that other types of medicament delivery member shields capable of protecting the medicament delivery member 20 and keeping it sterile, may be used, such as for example a flexible needle shield, or FNS.

Figure 3:
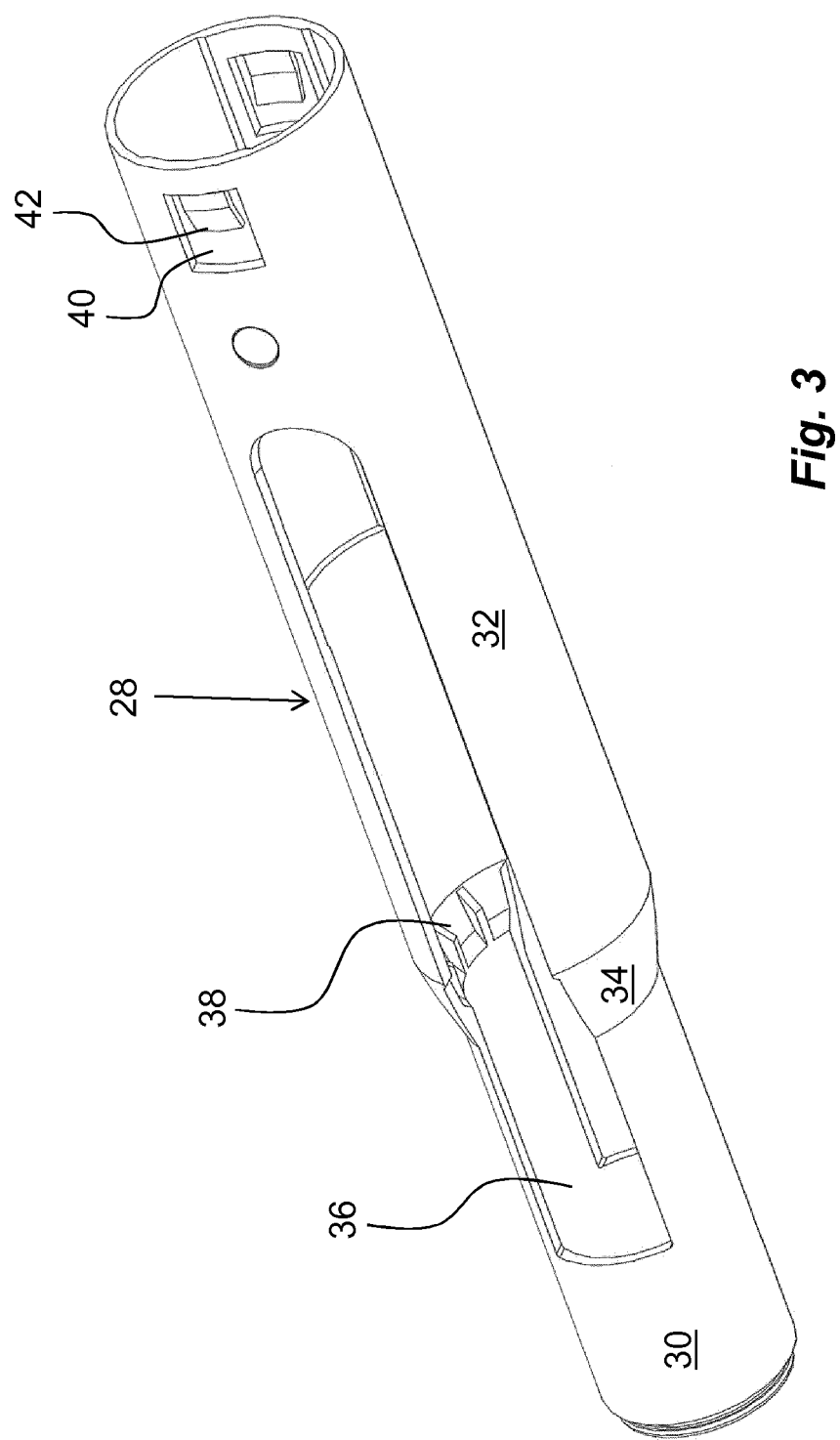

The proximal housing part 10 is further arranged with a central passage 26 at its proximal end, FIG. 1. An activation element, in the embodiment in the form of a medicament delivery member guard 28, FIGS. 1 and 3, is further coaxially and slidably arranged in the proximal housing part 10 and configured to extend through the central passage 26. The medicament delivery member guard 28 is generally tubular with a first proximal part 30 having a certain diameter and a second distal part 32 having a diameter larger than the proximal part 30, where these parts are joined by an intermediate conical section 34, FIG. 3. Two elongated cut-outs 36 are arranged along the medicament delivery member guard 28, on opposite sides thereof, also for viewing the medicament container 18. On the inner surface of the conical part a distally directed stop element 38, is arranged, FIG. 3, the function of which will be described below.

Figure 4:
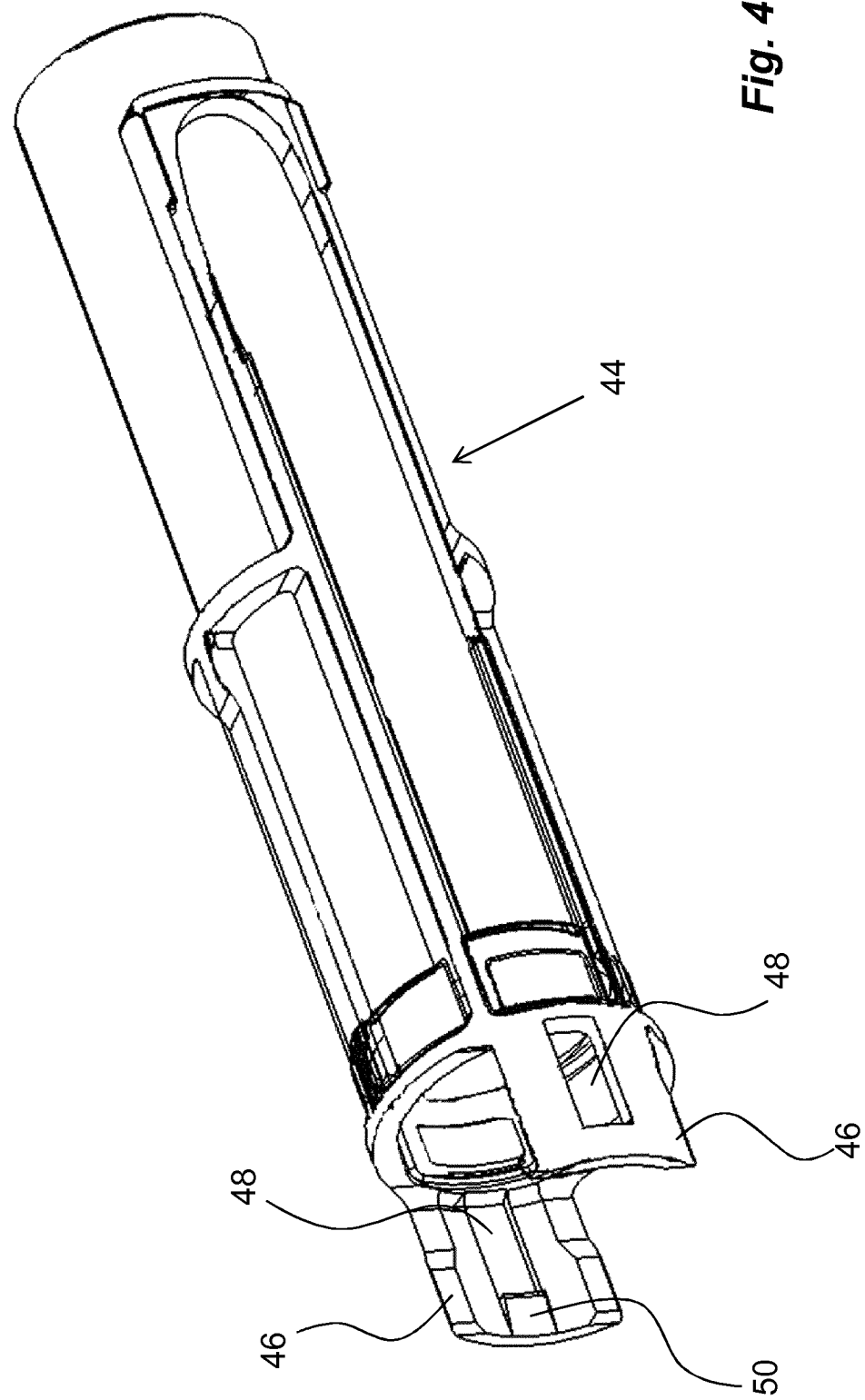

At the distal end of the medicament delivery member guard 28 two openings 40 are arranged opposite each other, where each opening 40 is arranged with a somewhat inwardly projecting, flexible, tongue 42, directed in the proximal direction. Further a medicament container holder 44 is arranged inside the medicament delivery member guard 28 in the form of a generally tubular body, FIGS. 1 and 4. Further, the distal end of the medicament container holder 44 is arranged with two distally directed tongues 46 where each tongue 46 is arranged with an opening 48 and an inwardly directed ledge 50 on the distal edge of each opening 48.

At the proximal end of the proximal housing part 10 a medicament delivery member shield remover 52 is arranged, FIG. 1. The medicament delivery member shield remover 52 has a generally tubular main body 54, which is arranged slidable onto the proximal end of the proximal housing part 10, wherein the proximal housing part is arranged with a section 56, FIG. 1, of a somewhat lesser diameter to accommodate the main body 54 and to be held there by friction. The medicament delivery member shield remover 52 is further arranged with a generally tubular removal element 58 which extends into the medicament delivery member guard 28 and surrounds the medicament delivery member shield 24. The removal element 58 is further arranged with proximally directed, inwardly inclined tongues 60 that are in contact with the outer surface of the medicament delivery member shield 24.

Figure 5:
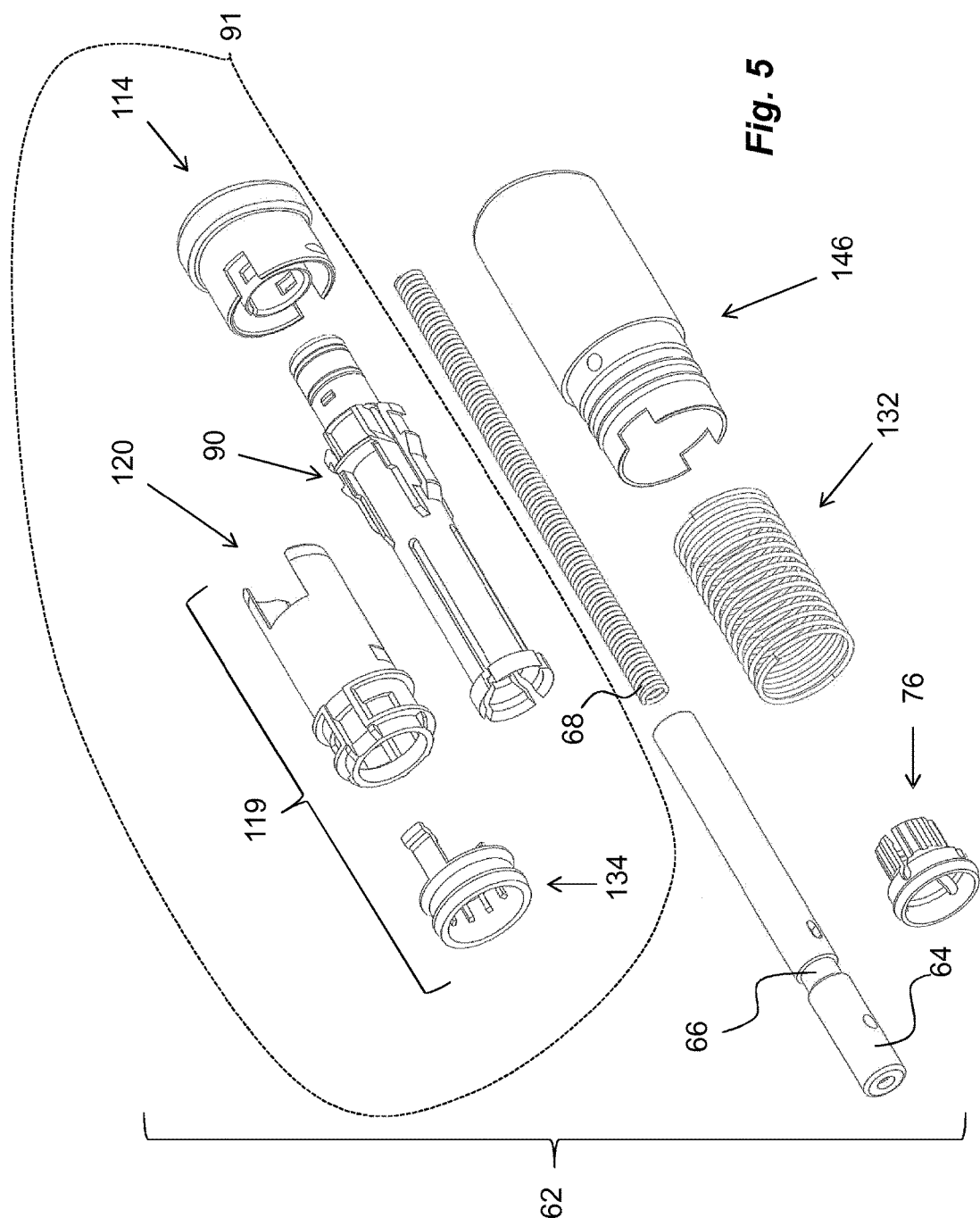
FIG. 5 is an exploded view of a power pack assembly comprised in the device of FIG. 1, FIGS. 6 to 10 are detailed views of components comprised in the power pack assembly of FIG. 5, FIG. 11a, b are longitudinal cross-sectional views of the power pack assembly of FIG. 5, and FIGS. 12 to 16 are cross-sectional view showing different functional states of the device of FIG. 1.

A power pack assembly 62 is shown in FIGS. 1, 5, 11a, b. The power pack assembly 62 comprises a plunger rod 64 extending along a longitudinal axis L and having a proximal and an opposite distal end. Further, the plunger rod 64 has a generally tubular shape and has an outer diameter somewhat smaller than the inner diameter of the medicament container 18 to be used. The plunger rod 64 is arranged with a circumferential groove 66, having a certain width.

The power pack assembly also comprises a first force element 68 arranged to exert a force on the plunger rod 64. In the shown embodiment the first force element 68 is a helical compression spring arranged inside the plunger rod 64. The first force element 68 is arranged between an end wall 72 at the proximal end of the plunger rod 64 and a proximally directed wall 74 of the actuator, FIG. 2b. Inside the first force element a spring guide 70 is placed, FIG. 2a.

Adjacent the circumferential groove 66 of the plunger rod 64, a container holder retainer 76 is arranged. It comprises a ring-shaped body 78 FIGS. 6 and 7, having an annular ledge 80 arranged around its circumference, which ledge 80 is arranged with a distally directed surface 81, and a number of flexible tongues 82 directed towards the distal end of the power pack assembly 62. Each tongue 82 is arranged with an inwardly directed ledge 84 arranged and shaped so as to fit into the groove 66 of the plunger rod 64 as seen in FIG. 11a. Each tongue 82 is further arranged with reinforcing ribs 88 on the outer surfaces thereof.

Further, the power pack assembly comprises an actuator 90 which is coaxially arranged on the plunger rod 64, FIGS. 5 to 8, which actuator 90 is designed with a mainly tubular body, having a central passage through which the plunger rod 64 fits. The actuator 90 comprises a holding element 96. In the present embodiment, the holding element 96 comprises a generally flexible tongue 100 having an inclined transition surface 92 which meets with a band-shaped part 94 with enlarged diameter and a radially extending inwardly directed ledge 95. In the present embodiment, the radially extending inwardly directed ledges 95 are configured to interact with the corresponding holding element 66 on the plunger rod 64. In the shown embodiment, the radially extending inwardly directed ledges 95 are arranged at the proximal end of the generally flexible tongues 100, formed by a number of longitudinally directed cut-outs 98. Each tongue 100 extends proximally along the longitudinal axis L and has the inclined outer transition surface 92 which meets with the band-shaped part 94 of a larger diameter. On the inner surface of each tongue 100 adjacent the transition surface 92, the radially extending inwardly directed ledge 95 is arranged, FIG. 8, having a shape so as to fit into the circumferential groove 66 of the plunger rod 64, as described above.

The actuator 90 is further provided with two stop ledges 102 directed radially outwards from the outer surface on either side. Between the stop ledges 102 two locking members 115 are arranged on the outer surface of the actuator 90, FIG. 8. In the shown embodiment, each locking member 115 comprises a radial flexible tongue 104 arranged with an outwardly directed hook 106 at the outer end, and a protrusion 108, having an inclined surface 110, extending a distance along each tongue 104. The radial flexible tongues extend distally along the longitudinal axis L. The distal end of the actuator 90 is arranged with an end wall 112. As shown in FIG. 2b, the first force element 68 is arranged between an end wall 72 at the proximal end of the plunger rod 64 and the end wall 112 of the actuator 90.

Figure 8:
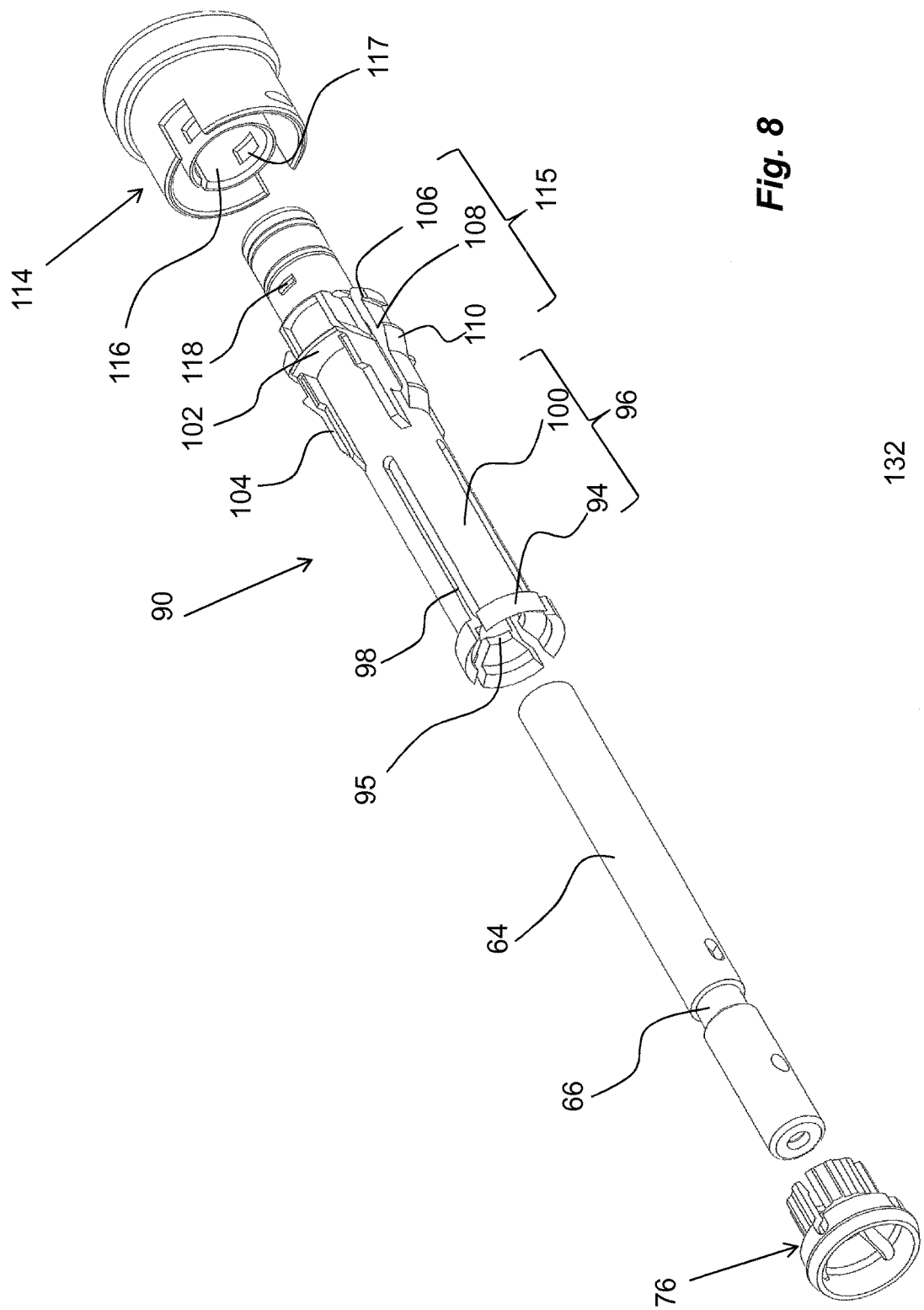

In the present embodiment, the power pack assembly further comprises an actuator button 114, FIG. 8, which is attached to the upper end of the actuator 90 by a proximally directed tubular post 116. The post 116 is arranged with sockets 117 on its inner surface, which sockets are configured to interact with radially directed protrusions 118 on an outer surface of the distal end of the actuator 90.

The power pack assembly also comprises an actuator sleeve mechanism 119, FIG. 5, arranged to releasably lock the radially extending inwardly directed ledges 95 of the actuator 90 in engagement with the corresponding holding element, i.e. the circumferential groove, of the plunger rod 64 so as to hold said first force element 68, i.e. the helical compression spring, in a tensioned state. The actuator sleeve mechanism 119 further comprises a tubular actuator cap 134 which is also configured to hold said radially extending inwardly directed ledges 95 in engagement with the corresponding holding element 66 of said plunger rod 64, and an actuator sleeve 120 interconnected with said actuator cap 134 such that said actuator cap 134 is moved a shorter distance in relation to the actuator 90 than the actuator sleeve 120 when said actuator sleeve is distally displaced in relation to the distal housing part.

In the present embodiment, the actuator sleeve 120 is slidably arranged in the longitudinal direction of the device and has generally tubular form. At its proximal end a first annular ledge 122 is arranged along the outer circumferential surface. A second annular ledge 124 is similarly arranged a further distance from the proximal end. The circumferential extension of the annular ledges 122, 124 is interrupted by two pairs of longitudinally extending ribs 126, connecting the first and second annular ledges 122, 124, and forming longitudinally extending passages on opposite sides of the actuator sleeve 120. Each passage is in turn arranged with proximally- and distally-facing walls, forming a compartment 128 in the passage. Further, the distal end of the actuator sleeve 120 is arranged with two oppositely arranged cut-outs 130 of a generally rectangular shape where the widths correspond to the width of the stop ledges 102 of the actuator 90. An inner surface of the actuation sleeve is arranged with a distally directed annular ledge 133 at its proximal area, FIGS. 2b and 9.

The actuator cap 134, FIGS. 5 and 9, is arranged coaxial with, and outside the actuator 90, proximally of the actuator sleeve 120. The actuator cap 134 has a ring-shaped body 136. A number of longitudinally extending ribs 138 are arranged on its inner surface, which ribs 138 are in contact with radially outwardly directed surfaces of the band-shaped part 94 of the actuator 90, where the function of the ribs 138 is to reduce the contact surface, i.e. the friction, with the band-shaped part 94. The outer surface of the body 136 is arranged with a circumferential ledge 140, which ledge 140 has a distally directed surface 142. The actuator cap 134 is further arranged with two distally extending tongues 144 placed on opposite sides of the circumference. Each distally extending tongue 144 is arranged with a radially inwardly directed protrusion 146 at its distal end. The radially inwardly directed protrusions 146 are then intended to fit into the compartments 128 of the actuator sleeve 120 wherein the protrusions 146 of the actuator cap 134 fit into the recesses 128. This arrangement enables a relative displacement in the longitudinal direction between the actuator cap 134 and the actuator sleeve 120, from a first position in which the radial inwardly directed protrusion 146 is in contact with a distal end surface 127 of the compartment 128 to a second position in which the radial inwardly directed protrusion 146 is in contact with a proximal end surface 129 of the compartment 128, FIG. 9.

The power pack assembly further comprises a distal housing part 148 of a generally tubular shape, FIGS. 5 and 10, where the proximal end of the distal housing part 148 has a somewhat lesser diameter, corresponding to the inner diameter of the distal end of the proximal housing part 10 and provided with a number of annular protrusions 150 which are intended to fit into the corresponding annular recesses 152, FIG. 2b, on the inner surface of the proximal housing part 10. On the inner circumferential surface of the distal housing part 148, a corresponding locking member 156 is arranged. This corresponding locking member is configured to interact with the locking member 115. The corresponding locking member 156 in the present embodiment is an annular ledge 154, which ledge 154 extends distally and is provided with a stop element having a shape for engaging to the hooks 106 of the actuator 90, FIG. 10.

The power pack assembly also comprises a second force element 132, FIGS. 5 and 11, shown as a second compression spring. Its function will be explained below. The second force element 132 is arranged between said actuator 90 and said actuator sleeve 120 and is configured to exert a force on said actuator sleeve. More particularly, the second force element 132 is positioned between a distally directed surface of the second annular ledge 124 of the actuator sleeve 120 and a proximally directed surface of the stop ledges 102 of the actuator 90, as seen in FIG. 11a.

When the power pack assembly is assembled, the plunger rod 64 is held against the force of the first force element 68 because the radially extending inwardly directed ledges 95 of the tongues 100 of the actuator 90 are situated in the holding element 66, i.e. the circumferential groove, of the plunger rod 64, and because the actuator cap 134 is positioned radially outside and in contact with the band-shaped parts 94 of the tongues 100, thereby preventing the tongues 100 from flexing radially outwards, as seen in FIG. 11b.

The hooks 106 of the locking member 115 of the actuator 90 are positioned adjacent the corresponding locking member 156, i.e. the circumferential ledge, of the distal housing part 148. In this position, if the actuator button 114 is depressed, it can move proximally together with the actuator 90 only a very short distance, until the hooks 106 engage the corresponding locking member 156, i.e. the circumferential ledge, of the distal housing part 148

Regarding the assembled proximal part of the medicament delivery device, a container holder retainer 76 is arranged adjacent the holding element 66 of the plunger rod 64. The container holder retainer 76 comprises a ring-shaped body 78, FIGS. 6 and 7, having an annular ledge 80 arranged around its circumference, which ledge 80 is arranged with a distally directed surface 81, and a number of flexible tongues 82 directed towards the distal end of the power pack assembly 62. Each tongue 82 is arranged with inwardly directed ledges 84 arranged and shaped so as to fit into the holding element 66, i.e. the groove, of the plunger rod 64 as seen in FIG. 11a. Each tongue 82 is further arranged with reinforcing ribs 88 on the outer surfaces thereof.

Figure 2:
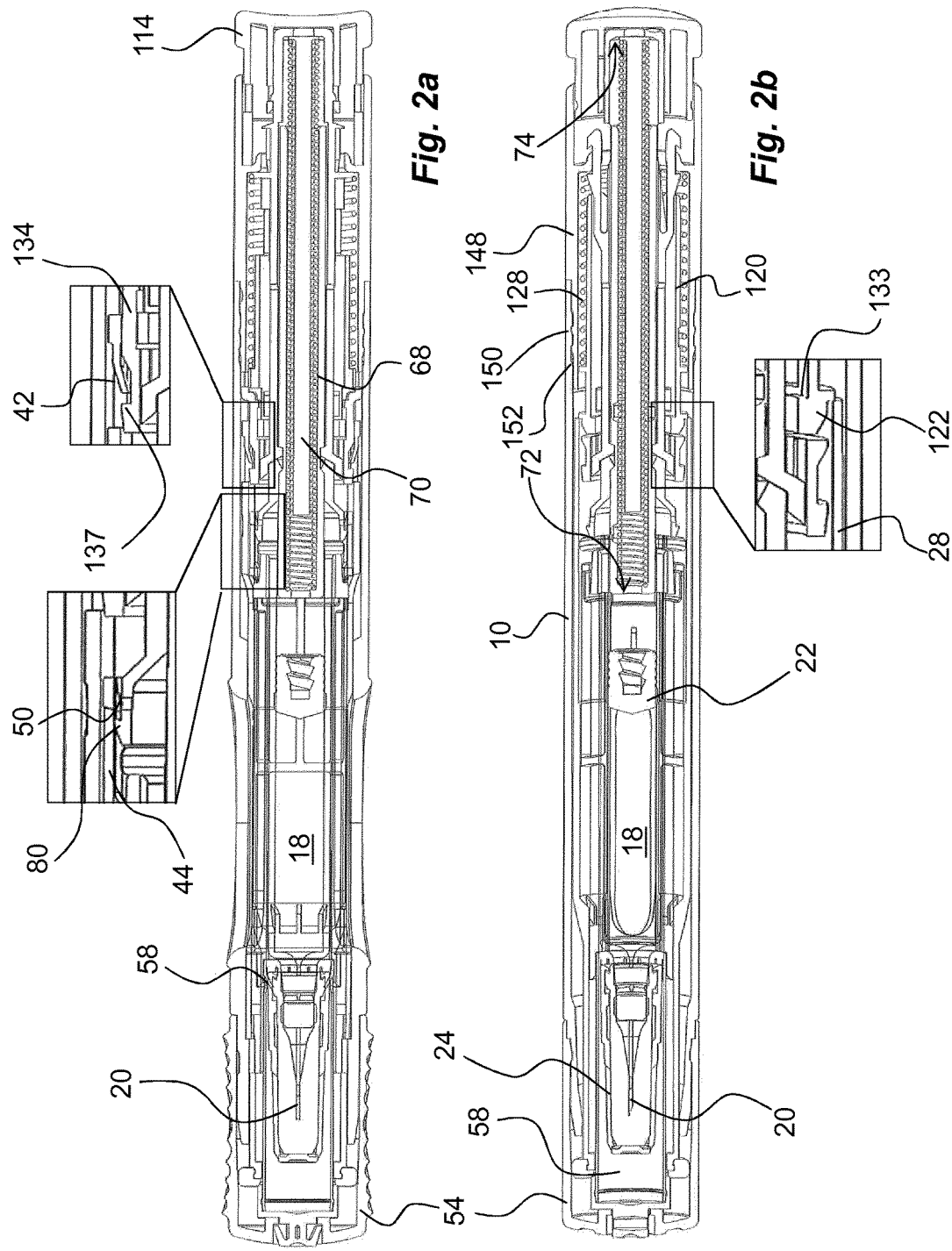

A medicament container 18 is placed in the medicament container holder 44 and the unit is placed in the proximal housing part 10. The power pack assembly 62 is attached to the proximal housing part 10 where the protrusions 150 of the distal housing part 148 fit into the recesses 152 of the proximal housing part 10, thereby locking the housing parts to each other. At the same time the tongues 42 of the medicament delivery member guard 28 fit behind the ledge 140 of the actuator cap 134, as seen in FIG. 2a. The distally directed end surface of the medicament delivery member guard 28 is in contact with proximally directed surface of the first annular ledge 122 of the actuator sleeve 120 as seen in FIG. 2. The ledges 50 of the medicament container holder 44 pass behind the annular ledge 80 of the container holder retainer 76 and in contact with the distally directed surface 81, FIG. 2a. The medicament delivery member shield remover 52 is inserted into the proximal end of the device. The device is now ready for use.

When a medicament delivery, more particularly an injection, is to be performed the medicament delivery member shield remover 52 is pulled out of the device. This causes the sharp pointed tongues 60 to grip into the outer surface of the medicament delivery member shield 24 and remove it from the medicament delivery member 20. The proximal end of the device is then pressed against a dose delivery site and the somewhat projecting proximal end of the medicament delivery member guard 28 is pushed distally relative to the proximal housing part, i.e. into the proximal housing part 10, FIG. 12, against the force of the second force element 132 acting between the second annular ledge 124 of the actuator sleeve 120 and the stop ledges 102 of the actuator 90. The distal end of the medicament delivery member guard 28 is in contact with the first annular ledge 122 of the actuator sleeve 120 and its movement in the distal direction also causes the actuator sleeve 120 to move in the distal direction.

The distally directed edge of the actuator sleeve 120 will then come in contact with the inclined surfaces 110 of the tongues 104 on the actuator 90 whereby the hooks 106 are moved radially inwards, causing a first frictional resistance, as seen in FIG. 12 and are free to pass inside the corresponding locking member 156, i.e. the circumferential ledge, of the distal housing part 148. Since the radially inwardly directed protrusion 146 of the distally extending tongues of the actuator cap 134 are in contact with the distal end surfaces 127 of the compartment 128, the distal movement of the actuator sleeve 120 will first cause a gap g, FIG. 12, between the actuator sleeve 120 and the actuator cap 134, corresponding to the length of the compartment 128, until the radial inwardly directed protrusions 146 of the distally extending tongues 144 of the actuator cap 134 make contact with the proximal end surfaces 129 of the compartment 128, whereby the actuator cap 134 will also be moved in the distal direction, along with the actuator sleeve 120 causing a second frictional resistance. As seen in FIG. 12, this will cause a certain length l of the band-shaped part 94 of the tongues 100 of the actuator 90 to be exposed. Thus, in relation to the actuator 90, the actuator sleeve mechanism described above will cause a shorter distal movement of the actuator cap 134 than of the actuator sleeve 120.

Should the user however remove the medicament delivery device from the dose delivery site, the second force element 132 will push the actuator sleeve 120 in the proximal direction and thereby push the medicament delivery member guard 28 proximally back to its original position. A subsequent press on the actuator button 114 will therefore not cause the device to be activated, unless the device is again pressed against an injection site. Since the actuator sleeve 120 is separate from the actuator cap 134, the movement of the actuator sleeve 120 in the proximal direction can be performed with very little frictional resistance since there is no relative movement between the contact surfaces of the band-shaped part 94 and the actuator cap 134 until the actuator cap has moved a distance g in the proximal direction. The only frictional resistance that the second force element 132 has to handle is the contact force between the inclined surface 110 of the protrusion 108 of the locking member 115 of the actuator 90 and the distally directed edge of the actuator sleeve 120, which friction is very small. Thereafter, the radially inwardly directed protrusion 146 of the distally extending tongues of the actuator cap 134 are again in contact with the distal end surfaces 127 of the compartment 128, causing the actuator sleeve 120 to push the cap along proximally, again giving rise to the second frictional resistance. Thus, since the frictional resistance is divided into two subsequent, non-overlapping steps, the risk that the actuator sleeve 120 should remain in the distal position, i.e. in the active state, leaving the device unlocked, is eliminated.

When activating the penetration and dose delivery, i.e. the injection, the user merely presses the actuator button 114, FIG. 13. Since the actuator button 114 is attached to the actuator 90, the actuator will move in the proximal direction whereby the hooks 106 will pass inside the corresponding locking member 156, i.e. the circumferential ledge, of the distal housing part 148 and the band-shaped part 94 of the actuator 90 will move completely out of the actuator cap 134 as seen in FIG. 13. The resilient properties of the tongues 100 of the actuator 90 causes the radially extending inwardly directed ledge 95 to move out of the holding element 66, i.e. out of the circumferential groove, of the plunger rod 64, FIG. 14. The plunger rod is then free to move in the proximal direction due to the force of the first force element 68.

The force of the first force element 68 urges the plunger rod 64 to act on the stopper 22 of the medicament container 18. But because of the friction between stopper 22 and the container wall and the incompressibility of the liquid in the medicament container 18 and also because of the narrow channel through the medicament delivery member 20, no liquid will be expelled at this stage. Instead, the spring force will push the medicament container and the medicament container holder in the proximal direction, and thereby cause the delivery member 20, i.e. the needle, to penetrate the skin of the patient, FIG. 14.

The penetration movement stops when a proximally directed surface of the medicament container holder 44 surrounding the neck portion abuts the stop element 38 of the medicament delivery member guard 28. The halted medicament container holder 44 and the continued push of the plunger rod 64, will cause the ledges 84 of the container holder retainer 76 to be forced out of the holding element 66, i.e. the circumferential groove, of the plunger rod 64, because the arms 82 of the container holder retainer 76 are no longer held in place by the band-shaped part 94 of the actuator 90.

With the plunger rod released to move relative to the medicament container 18, the force from the first force element 68 urges the plunger rod 64 to move the stopper 22 relative to the medicament container 18. The liquid medicament is thereby delivered to the patient until the stopper 22 reaches the inner proximal end of the medicament container 18, FIG. 15. After moving this distance, the distal end of the plunger rod 64 has passed the radially extending inwardly directed ledge 95 of the actuator 90, and the tongues 100 are moved radially inwards, FIG. 15. A remaining force of the first force element 68, forces the actuator 90 to move towards the distal end whereby the two stop ledges 102 of the actuator 90 hits the annular distally directed ledge 154 of the distal housing part and thus a feedback audible signal is produced. This signal advises the user that the dose has been completely delivered.

Because the second force member 132 is acting on the actuator sleeve 120 it is urged in the proximal direction. Therefore, when the device is removed from the injection site, the force of the second force member 132 pushes the actuator sleeve 120 and thus the medicament delivery member guard 28 connected to it in the proximal direction, whereby the medicament delivery member guard 28 is pushed out of the proximal end of the proximal housing part 10 and surrounds the medicament delivery member 20, FIG. 16a. The movement of the actuator sleeve 120 causes the band-shaped part 94 of the actuator 90 to pass the annular ledge 133 on the inner surface of the actuator sleeve 120, FIG. 16b. This ledge 133 prevent any attempts to push the medicament delivery member guard 28 back into the device because the ledge will abut the proximal end of the band-shaped part 94 of the actuator 90. The medicament delivery member guard is thereafter permanently locked.

Further, when the actuator button 114 is released, it will move distally back into its initial position together with the actuator 90 due to a remaining force from the first force member 68. The radially flexible tongues 104 of the actuator 90 will then flex back radially outwards whereby the hooks 106 will come into contact with the corresponding locking member 156, i.e. the circumferential ledge, of the distal housing part 148. The actuator button is thus also locked as seen in FIG. 16b.

As a safety measure, it is not possible to first press the actuator button 114 and then press the medicament delivery member guard 28 against a delivery site in order to release the penetration/dose delivery action, because a manual pressure on the actuator button causes the hooks 106 to engage the with the corresponding locking member 156, i.e. the circumferential ledge, of the distal housing part 148, which in turn prevents the radially flexible tongues 104 from flexing inwards should the medicament delivery member guard 28 be pressed against an injection site. In order to release a penetration/dose delivery action, the medicament delivery member guard 28 has to be held pressed against an injection site in order to be able to depress the actuator button and release the plunger rod.

In a further embodiment (not shown) the hooks 106 are removed such that the sequence for activation is independent i.e. the penetration/delivery action is either released by first pressing the actuator button and then the medicament delivery member guard 28 against the delivery site, or by first pressing the medicament delivery member guard 28 against the delivery site and then pressing the actuator button.

It is to be understood that the embodiment described above and shown in the drawings is to be regarded only as a non-limiting embodiment of the invention and that it may be modified in many ways within the scope of the patent claims.

The invention claimed is:

1. A power pack assembly for a medicament delivery device, the power pack comprising:
 a plunger rod extending along a longitudinal axis (L) and having a proximal and an opposite distal end,
 an actuator provided with a holding element and configured to interact with a corresponding holding element of the plunger rod,
 a first force element arranged to exert a force on the plunger rod,
 an actuator sleeve mechanism arranged to releasably lock the holding element in engagement with the corresponding holding element of the plunger rod such as to hold the first force element in a tensioned state, wherein the actuator sleeve mechanism comprises an actuator cap configured to hold the holding element in engagement with the corresponding hold element of the plunger rod, and in that an actuator sleeve is interconnected with the actuator cap such that in relation to the actuator, the actuator cap is moved a shorter distance than the actuator sleeve when the actuator sleeve is distally displaced in relation to the distal housing part.

2. A power pack assembly according to claim 1, wherein the actuator sleeve mechanism further comprises a second force element configured to exert a force on the actuator sleeve.

3. A power pack assembly according to claim 2, wherein the second force element is arranged between the actuator and the actuator sleeve.

4. A power pack assembly according to claim 1, wherein the actuator cap and the actuator sleeve are slidably arranged in relation to each other.

5. A power pack assembly according to claim 1, wherein the power pack assembly further comprises distal housing part in which the actuator is slidably arranged.

6. A power pack assembly according to claim 1, wherein the actuator cap and the actuator sleeve are interconnected by a distally extending tongue provided with a radial inwardly directed protrusion which fits into a compartment on the actuator sleeve.

7. A power pack assembly according to claim 6, wherein the compartment is configured to allow a relative displacement between the actuator cap and the actuator sleeve from a first position in which the radial inwardly directed protrusion is in contact with a distal end surface of the compartment to a second position in which the radial inwardly directed protrusion is moved in contact with a proximal end surface of the compartment upon distal displacement of the actuator sleeve.

8. A power pack assembly according to claim 7, wherein the actuator comprises a locking member confined to interact with a corresponding locking member of the distal housing part.

9. A power pack assembly according to claim 8, wherein the locking member is configured for locking a proximal displacement of the actuator until the actuator sleeve is distally displaced in relation to the distal housing part.

10. A power pack assembly according to claim 9, wherein the actuator sleeve is configured to interact with the locking member of the actuator when the actuator sleeve is distally displaced such that the actuator is allowed to be proximally displaced.

11. A power pack assembly according to claim 10, wherein the proximal displacement of the actuator allows the holding element of the actuator to be released from the actuator cap such that the engagement between the holding element of the actuator and the corresponding holding element of the plunger rod is released.

12. A power pack assembly according to claim 11, wherein the first force element is released from the tensioned state forcing the plunger rod to be proximally displaced.

13. A power pack assembly according to claim 12, wherein the locking member of the actuator comprises a radial flexible tongue arranged with an outwardly directed hook at the outer end.

14. A power pack assembly according to claim 13,
wherein the locking member of the actuator comprises a protrusion with an inclined surface extending a distance along the radially flexible tongue; and
wherein the corresponding locking member of the distal housing part comprises an annular distally directed ledge.

15. A power pack assembly according to claim 14,
wherein the actuator sleeve comprises a distally directed edge arranged to interact with the inclined surface whereby,
upon distal displacement of the actuator sleeve, the radially flexible tongue with the hook is moved radially inwards such that the outwardly directed hook is free to pass inside the annular distally directed ledge of the distal housing part.

16. A power pack assembly according to claim 1,
wherein the holding element comprises a generally flexible tongue having an inclined transition surface which meets with a band-shaped part with enlarged diameter and an radially extending inwardly directed ledge.

17. A power pack assembly according to claim 16, wherein the corresponding holding element of the plunger rod comprises a circumferential groove, having a mutual shapes so as to fit the radially extending inwardly directed ledge in the circumferential groove.

18. A power pack assembly according to claim 16,
wherein the radially extending inwardly directed ledge is arranged at the inner end of the generally radially flexible tongue of the actuator.

19. A power pack assembly according to claim 18,
wherein the actuator cap comprises a ring shaped body having an inner diameter generally corresponding to the radial extension of the holding element in the area of the band-shaped part.

20. A medicament delivery device comprising a power pack assembly comprising
a plunger rod extending along a longitudinal axis (L) and having a proximal and an opposite distal end,
an actuator provided with a holding element and configured to interact with a corresponding holding element of the plunger rod,
a first force element arranged to exert a force on the plunger rod,
an actuator sleeve mechanism arranged to releasably lock the holding element in engagement with the corresponding holding element of the plunger rod such as to hold the first force element in a tensioned state, wherein
the actuator sleeve mechanism comprises an actuator cap configured to hold the holding element in engagement with the corresponding hold element of the plunger rod, and in that an actuator sleeve is interconnected with the actuator cap such that in relation to the actuator, the actuator cap is moved a shorter distance than the actuator sleeve when the actuator sleeve is distally displaced in relation to the distal housing part.

* * * * *